United States Patent [19]

Davis et al.

[11] Patent Number: 4,894,461
[45] Date of Patent: Jan. 16, 1990

[54] 3-(γ-CHLOROPROPYL)-6-FLUORO-1,2-BENZISOXAZOLE

[75] Inventors: Larry Davis, Sergeantsville; Richard C. Effland, Bridgewater, both of N.J.

[73] Assignee: Hoechst-Roussel Pharmaceuticals, Inc., Somerville, N.J.

[21] Appl. No.: 833,587

[22] Filed: Feb. 27, 1986

Related U.S. Application Data

[63] Continuation of Ser. No. 257,698, Apr. 27, 1981, abandoned.

[51] Int. Cl.⁴ .............................................. C07D 31/42
[52] U.S. Cl. .................................. 548/241; 546/198; 564/254; 568/337
[58] Field of Search .................. 548/241; 564/254; 544/401

[56] References Cited

U.S. PATENT DOCUMENTS

| | | | |
|---|---|---|---|
| 3,629,239 | 12/1971 | Kitabonoki et al. | 564/254 |
| 3,732,306 | 5/1973 | Gutman et al. | 564/254 |
| 3,951,999 | 4/1976 | Saunders et al. | 548/241 |
| 3,960,951 | 6/1976 | Gutman | 564/254 |
| 4,007,227 | 2/1977 | Baker et al. | 564/254 |
| 4,128,580 | 12/1978 | Matsumoto et al. | 564/254 |
| 4,172,896 | 10/1979 | Hitoshi et al. | 548/241 |
| 4,235,914 | 11/1980 | Sasajima et al. | 544/401 |
| 4,458,075 | 7/1984 | Davis et al. | 548/241 |
| 4,604,395 | 8/1986 | Davis et al. | 548/241 |

FOREIGN PATENT DOCUMENTS

| | | | |
|---|---|---|---|
| 684398 | 3/1965 | Italy | 564/254 |
| 9070963 | 7/1974 | Japan | |
| 1136666 | 11/1976 | Japan | |
| 3077057 | 7/1978 | Japan | 548/241 |

OTHER PUBLICATIONS

Noller, Carl; *Textbook of Organic Chemistry*, p. 169 (1966).
Katritsky and Boulton; *Advances in Heterocyclic Chemistry*, vol. 8, pp. 283–286, (1967).
Uno et al.; "3-Substituted 1,2 Benzisoxazole Derivatives", *Chem Pharm. Bull.* 24 (4), 632–643, (1976).

*Primary Examiner*—Mukund J. Shah
*Assistant Examiner*—E. Bernhardt
*Attorney, Agent, or Firm*—Elliott Korsen; Jerome Rosenstock

[57] ABSTRACT

3-(γ-chloropropyl)-6-fluoro-1,2-benzisoxazole is a compound useful in preparing compounds having a neuroleptic utility. The benzisoxazole is prepared by cyclizing an oxime derivative having the formula

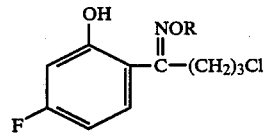

where R is a substituent selected from

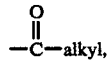

where alkyl is a straight or branched chain hydrocarbon of 1 to 6 carbon atoms, and

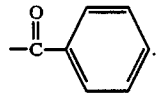

1 Claim, No Drawings

3-(γ-CHLOROPROPYL)-6-FLUORO-1,2-BENZISOXAZOLE

This application is a continuation of application Ser. No. 257,698, filed Nov. 27, 1981, abandoned.

This invention is directed to 3-(γ-chloropropyl)-6-fluoro-1,2-benzisoxazole, having a structure formula of

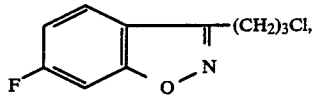

which is useful in the synthesis of compounds which have utility as neuroleptics.

Japanese patent publication J5 1136-666 discloses a broad class of compounds of the formula I as starting materials for drugs exhibiting action on the central nervous system,

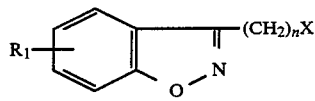

I where $R_1$ is hydrogen, halogen atom, lower alkoxy, or hydroxy; X is a reactive ester residue of an alcohol (e.g., chlorine, bromine, iodine, an aryl sulfonyloxy group, such as p-toluenesulfonyloxy or benzene sulfonyloxy, or an alkyl sulfonyloxy group, such as methanesulfonyloxy; and n is an integer 1-3.

This disclosure, however, does not reveal or hint that 3-(γ-chloropropyl)-6-fluoro-1,2-benzisoxazole is especially useful in the synthesis of neuroleptics, nor does it reveal or hint at the preparation of this precursor or a method by which to do so.

Japanese patent publication J4 9070 963 describes the preparation of 1,2-benzisoxazole derivatives of formula II,

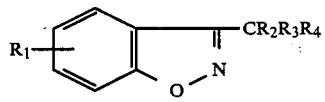

II where $R_1$ is hydrogen, hydroxy, alkoxy, alkyl, halogen, nitro;

$R_2$ is halogen; $R_3$ is hydrogen, halogen; $R_4$ is hydrogen, halogen, carboxyl, alkoxycarbonyl by halogenating 1,2-benzisoxazole-3-acetic acid derivatives III,

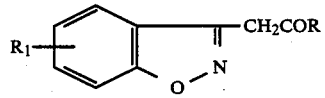

III where R is hydroxy, alkoxy, halogen; and $R_1$ is as shown under II.

No method, however, is revealed or hinted at which would yield 3-(γ-chloropropyl)-6-fluoro-1,2-benzisoxazole of this invention or even closely related analogs or next adjacent homologs.

A process for preparation of a 3-(γ-substituted propyl)-6-fluoro-1,2-benzisoxazole is described. The process comprises cyclizing an oxime having the formula

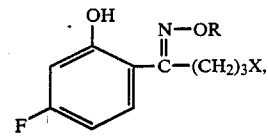

where X is a leaving group in organic nucleophilic displacement reactions. Typical leaving groups are a halide group, comprising Cl and Br, a tosyl group, a mesyl group, etc. A preferred halide is Cl. R is a substituent selected from

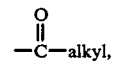

where alkyl is a straight or branched chain hydrocarbon of 1 to 6 carbon atoms, and

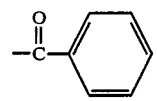

The starting compound for the preparation of 3-(γ-substituted-propyl)-6-fluoro-1,2-benzisoxazole is γ-substituted-4-fluoro-2-hydroxybutyrophenone. A preferred compound is γ-chloro-4-fluoro-2-hydroxybutyrophenone having a formula,

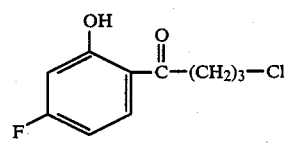

A butyrophenone precursor to this benzisoxazole is prepared by reacting 3-fluorophenol, with an acid chloride, such as the acid chloride

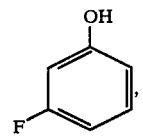

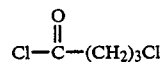

in the manner described in Belgian patent 839,097.

The resultant butyrophenone, e.g. γ-chloro-4-fluoro-2-hydroxybutyrophenone, is then converted into its oxime, e.g.

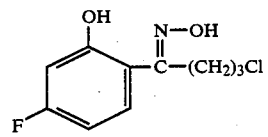

by reaction with a salt of hydroxylamine, utilizing conventional techniques and conditions. Typically, hydroxylamine hydrochloride is employed in the presence of an acid acceptor, such as pyridine.

The resulting oxime, γ-chloro-4-fluoro-2-hydroxybutyrophenone oxime, is predominantly the E-oxime in respect to its position relative to the benzene ring. This reasoning is deduced from the fact that after acetylation to E-γ-chloro-4-fluoro-2-hydroxybutyrophenone-0-acetyl oxime, the acetylated oxime gives a high yield (80%) of 3-(γ-chloropropyl)-6-fluoro-1,2-benzisoxazole on cyclization.

The resulting oxime, e.g.

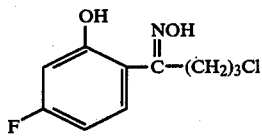

is reacted with an acyl anhydride, acetyl halide, e.g., chloride, or benzoic anhydride or halide to form an 0-acetyl or 0-benzoyl compound, e.g.

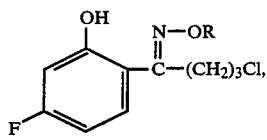

where R is selected from

alkyl, where alkyl is a straight or branched chain hydrocarbon substituent having 1 to 6 carbon atoms, and

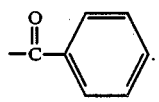

It is to be understood that other reagents reacting with the —OH group of the oxime may be employed to form 0-alkanoyl or 0-aroyl derivatives, as for example, propionic anhydride, butyric anhydride, acetic benzoic anhydride, propionyl chloride, butyroyl chloride, and benzoyl chloride.

The resulting 0-alkanoyl or 0-aroyl derivative is then cyclized in the presence of a base to form the desired compound

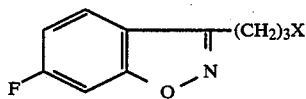

e.g., 3-(γ-chloropropyl)-6-fluoro-1,2-benzisoxazole. Typically the cyclization is carried out in the presence of potassium carbonate.

Alternate reagents to potassium carbonate to effect cyclization of the 0-acyl oxime, e.g., E-γ-chloro-4-fluoro-2-hydroxybutyrophenone-0-acetyl oxime, include alkaline reagents such as sodium bicarbonate, sodium carbonate, calcium carbonate, magnesium carbonate, calcium oxide, magnesium oxide and potassium hydroxide. Because of the necessity to avoid excess alkali with its potential for reaction with the chlorine atom of the chloropropyl side chain attached to the benzisoxazole ring, it is desirable to limit any alkali present to a slight excess over that required to react with the phenol group. Desirably, alkali remaining after reaction with the acetylated oxime should not cause a pH greater than 9 after dilution with water. Cyclization with reagents yielding a pH after reaction and dilution with water below 8 are preferred.

It is understood that the above-identified reactions of the reaction sequence are carried out in a conventional solvent system typically employed therefor and well known to those skilled in the art.

The overall reaction sequence from γ-chloro-4-fluoro-2-hydroxy-butyrophenone to its oxime to its acetylated oxime to 3-(γ-chloropropyl)-6-fluoro-1,2-benzisoxazole is remarkable for its high yield of desired product. This yield is the more remarkable in that the γ-chloropropyl group survives intact and is available for subsequent use in reactions to prepare compounds having neuroleptic utility, such as for example 4-(4-chlorophenyl)-1-[3-(6-fluoro-1,2-benzisoxazole-3-yl)propyl]-4-hydroxypiperidine.

Neuroleptic activity is demonstrated by a climbing mice assay. Apomorphine induces climbing in mice at low dose levels which do not induce oral stereotypy or motor stimulation. This effect of apomorphine is antagonized by neuroleptics, so this test is an additional screen for neuroleptic drugs.

The procedure is as follows. The subjects are CD-1 male mice (23–27 grams), group-housed under standard laboratory conditions. The mice are individually placed in wire mesh stick cages (4"×4"×10") and are allowed one hour for adaptation and exploration of the new environment. Apomorphine is then injected subcutaneously at 1.5 mg/kg, a dose causing climbing in all subjects for 30 minutes. Compounds to be tested for neuroleptic activity are injected intraperitoneally 30 minutes prior to the apomorphine challenge at a screening dose of 10 mg/kg.

For evaluation of climbing, 3 readings are taken at 10, 20 and 30 minutes after apomorphine administration according to the following scale:

| Climbing Behavior | Score |
|---|---|
| Mice with: | |
| 4 paws on bottom (no climbing) | 0 |
| 2 paws on the wall (rearing) | 1 |
| 4 paws on the wall (full climb) | 2 |

Mice consistently climbing before the injection of apomorphine will be discarded.

With fully-developed apomorphine climbing, the animals are hanging onto the cage walls, rather motionless, over longer periods of time. By contrast, climbs due to mere motor stimulation usually only last a few seconds.

The climbing scores are individually totaled (maximal score: 6 per mouse over 3 readings) and the total score of the control group (vehicle intraperitoneally)-apomorphine s.c.) is set to 100%. $ED_{50}$ values with 95% confidence limits are calculated by a Linear Regression Analysis.

The compound 4-(4-chlorophenyl)-1-[3-(6-fluoro-1,2-benzisoxazole-3-yl)propyl]-4-hydroxypiperidine produces a 50% inhibition of the climbing response induced by a 1.5 mg/kg. subcutaneous dose of apomorphine at doses of 0.51 mg/kg (intra peritoneally) or 0.77 mg/kg (orally).

The teachings of this invention are shown by the following examples:

In view of the amendments to the Manual of Patent Examining Procedure, including Sections 608.01(p); 707.07(1); 2004; 2012 dated January. 1981 and received on or about the week of Sept. 14, 1981, Examples I to 5 of the specification are to be read as if they were expressed in the past tense since they are examples which have actually been carried out.

EXAMPLE I

γ-Chloro-4-fluoro-2-hydroxybutyrophenone

To 350 ml. (2.8 mole) cold boron trifluoride etherate is added 100 g. (0.89 mole) of 3-fluorophenol and 252 g. (200 ml. 1.78 mole) of 4-chlorobutyryl chloride. The resulting solution is stirred for twenty hours at 130° C.

The mixture is cooled and poured into one liter of mixed ice and water. After stirring for ten minutes, the water mixture is extracted three times with 200 ml. of ether each time. The ether extracts are combined an and washed three times with water. The ether extract is dried by washing with a saturated solution of sodium chloride in water and is then of dilute dried over anhydrous magnesium sulfate.

The magnesium sulfate is filtered from the dry ether solution and the ether is evaporated. The resultant oil is vacuum distilled and a fraction is collected at 110°-150° C. (1.0 mm., pot at 170°-250° C.) weighing 115 g. (60% of the theoretical yield). This material is recrystallized from a mixed solvent solution (hexane/ether at 8:1 ratio) to obtain white crystals of γ-chloro-4-fluoro-2-hydroxybutyrophenone, melting at 68°-70° C.

EXAMPLE 2

E-γ-chloro-4-fluoro-2-hydroxybutyrophenone oxime

To 25 ml. of pyridine is added 11.2 g. (0.052 mole) of γ-chloro-4-fluoro-2-hydroxybutyrophenone of Example 1 and 4.14 g. (0.06 mole) of hydroxylamine hydrochloride. This mixture is stirred overnight (20 hours) at ambient temperature. It is then poured into 100 ml. of dilute hydrochloric acid, stirred for five minutes, and is extracted with ether. The ether solution is washed two times with water before it is dried by washing with a saturated solution of sodium chloride in water followed by final drying over anhydrous magnesium sulfate.

The magnesium sulfate is filtered from the ether solution, and the ether is evaporated. The white solid obtained is recrystallized from a mixed hexane and ether solvent to obtain 11.5 g. (95% of the theoretical yield) of white crystals melting at 68°-70° C. A sample of this material is again recrystallized from hexane/ether to yield white crystals of E-γ-chloro-4-fluoro-2-hydroxybutyrophenone oxime, melting at 74°-6° C.

Analysis: Calculated for $C_{10}H_{11}ClFNO_2$: 51.84%C, 4.79%H, 6.05%N. Found: 52.20%C, 4.77%H, 6.00%N.

EXAMPLE 3

E-γ-chloro-4-fluoro-2-hydroxybutyrophenone-0-acetyl oxime

To 5.5 ml. (0.06 mole) of acetic anhydride is added 10.0 g. (0.043 mole) of E-γ-chloro-4-fluoro-2-hydroxybutyrophenone oxime.

This mixture is heated at 60° C. for one and one-half hours. The resulting mixture is cooled to room temperature and is dissolved in 100 ml. of ether. The ether solution is washed twice with a sodium bicarbonate solution in water. It is then washed twice with water. The ether solution remaining is dried by washing with a saturated solution of sodium chloride in water before finally drying it over anhydrous magnesium sulfate.

The magnesium sulfate is removed by filtration after drying is complete and the ether is evaporated from the dry ether solution to give a solid which is recrystallized from a mixed hexane/ether solvent to obtain 9.0 g. (76% of the theoretical yield) of E-γ-chloro-4-fluoro-2-hydroxybutyrophenone-0-acetyloxime possessing a melting point of 84°-87° C. A sample of this material is recrystallized from a mixed hexane/ether solvent. The crystals of E-γ-chloro-4-fluoro-2-hydroxybutyrophenone-0-acetyloxime which are obtained melt at 86°-88° C.

Analysis: Calculated for $C_{12}H_{13}ClFNO_3$: 52.66%C, 4.79%H, 5.12%N. Found: 52.56%C, 4.81%H, 5.05%N.

EXAMPLE 4

3-[γ-chloropropyl-6-fluoro-1,2-benzisoxazole

The cyclization of the acetylated oxime of Example 3 is effected by adding 6.5 g. (0.024 mole) of E-γ-chloro-4-fluoro-2-hydroxy-butyrophenone-0-acetyl oxime to 20 ml. of dry dimethylformamide (DMF) and 4.14 g. (0.03 mole) of potassium carbonate. This mixture is stirred for five hours at room temperature. It is poured into 500 ml. of water, stirred for five minutes, and is then extracted with a mixed solvent of ether/ethyl acetate. The extracted organic layer is washed two times with water and once with a saturated solution of sodium chloride in water. The organic layer is finally dried over anhydrous magnesium sulfate.

After drying, the magnesium sulfate is removed by filtration and the solution is evaporated to remove ether and ethyl acetate. The product is an oil. This oil is distilled to yield 4.0 g. (80% of the theoretical yield) of an oil of 3-(γ-chloropropyl)-6-fluoro-1,2-benzisoxazole boiling at 130° C./0.5 mm.

Analysis: Calculated for $C_{10}H_9ClFNO$: 56.22%C, 4.25%H, 6.56%N. Found: 56.21%C, 4.25%H, 6.52%N.

EXAMPLE 5

4-(4-Chlorophenyl-1-[3-(6-fluoro-1,2-benzisoxazole-3-yl)propyl]-4-hydroxypiperidine In 30 ml. dry DMF is added 4-(4-chlorophenyl)-4-hydroxypiperidine (3.0 g. 0.014 mole), 3-(γ-chloropropyl)-6-fluoro-1,2-benzisoxazole (2.99 g, 0.014 mole), $NaHCO_3$ (8.0 g, 0.1 mole), and 0.01 g. of KI. After stirring at 90° C. for one hour, the mixture is evaporated to an oil, which is stirred with 100 ml water for five minutes and then extracted with ether. The ether solution is washed twice with water and then dried (saturated NaCl, anhydrous $MgSO_4$). After filtering, the solvent is evaporated to yield 4.7 g of a solid, m.p. 130° C. The solid material is recrystallized from ether to yield 3.5 g (64%) m.p. 143°-5° C. This material is recrystallized from ether to yield 3.0 g of a solid of 4-(4-chlorophenyl)-1-[3-(6-fluoro-1,2-benzisoxazole-3-yl)propyl]-4-hydroxypiperidine, m.p. 148°-50° C.

Analysis: Calculated for $C_{21}H_{22}ClFN_2O_2$: 64.86%C, 5.70%H, 7.21%N. Found: 64.75%C, 5.64%H, 7.15%N.

We claim:

1. The compound 3-(γ-chloropropyl)-6-fluoro-1,2-benzisoxazole.

* * * * *